United States Patent
Trigueiros Da Silva Cunha et al.

(10) Patent No.: US 10,885,361 B2
(45) Date of Patent: Jan. 5, 2021

(54) BIOMETRIC METHOD AND DEVICE FOR IDENTIFYING A PERSON THROUGH AN ELECTROCARDIOGRAM (ECG) WAVEFORM

(71) Applicant: INESC TEC—INSTITUTO DE ENGENHARIA DE SISTEMAS E COMPUTADORES, TECNOLOGIA E CIÊNCIA, Oporto (PT)

(72) Inventors: João Paulo Trigueiros Da Silva Cunha, Oporto (PT); Joana Isabel Santos Paiva, Oporto (PT)

(73) Assignee: INESC TEC—INSTITUTO DE ENGENHARIA DE SISTEMAS E COMPUTADORES, TECHNOLOGIA E CIENA, Oporto (PT)

( * ) Notice: Subject to any disclaimer, the term of this patent is extended or adjusted under 35 U.S.C. 154(b) by 137 days.

(21) Appl. No.: 16/097,476

(22) PCT Filed: Apr. 28, 2017

(86) PCT No.: PCT/IB2017/052499
§ 371 (c)(1),
(2) Date: Oct. 29, 2018

(87) PCT Pub. No.: WO2017/187422
PCT Pub. Date: Nov. 2, 2017

(65) Prior Publication Data
US 2019/0147277 A1    May 16, 2019

(30) Foreign Application Priority Data
Apr. 29, 2016    (PT) .......................................... 109357

(51) Int. Cl.
*G06K 9/00* (2006.01)
*G06F 21/32* (2013.01)
(Continued)

(52) U.S. Cl.
CPC ........ *G06K 9/00885* (2013.01); *A61B 5/0472* (2013.01); *A61B 5/117* (2013.01);
(Continued)

(58) Field of Classification Search
CPC ....... A61B 5/0472; A61B 5/117; G06F 21/32; G06K 2009/00939; G06K 9/00503;
(Continued)

(56) References Cited

U.S. PATENT DOCUMENTS 7,988,561 B1    8/2011    Lenkarski et al.
8,132,127 B2    3/2012    Baier et al.
(Continued)

FOREIGN PATENT DOCUMENTS

EP    3056138 A2    8/2016

OTHER PUBLICATIONS

Keshishzadeh, Sarineh, and Saeid Rashidi. "A system of biometric authentication based on ECG signal segmentation." 2014 22nd Iranian Conference on Electrical Engineering (ICEE). IEEE, 2014. (Year: 2014).*

(Continued)

*Primary Examiner* — Nirav G Patel
(74) *Attorney, Agent, or Firm* — Leason Ellis LLP

(57) ABSTRACT

Method for identifying a person through an electrocardiogram, ECG, waveform, said method comprising: capturing ECG signals from a sample population including the person to be identified; computing sample population ECG distances ST, RT and QT from the captured ECG signals; training a computer classification model on the computed sample population ECG distances, provided that no other
(Continued)

ECG distances are used; capturing an ECG signal from the person to be identified; computing the person's ECG distances ST, RT and QT from the person's captured ECG signal; using the classification model with the person's computed ECG distances to identify the person to be identified within the sample population. Device for identifying a person through an electrocardiogram, ECG, waveform, said device comprising means for carrying out said method.

17 Claims, 5 Drawing Sheets

(51) Int. Cl.
*H04L 29/06* (2006.01)
*G06N 20/10* (2019.01)
*A61B 5/0472* (2006.01)
*A61B 5/117* (2016.01)
*G06K 9/62* (2006.01)

(52) U.S. Cl.
CPC ......... *G06F 21/32* (2013.01); *G06K 9/00503* (2013.01); *G06K 9/00536* (2013.01); *G06K 9/6269* (2013.01); *G06N 20/10* (2019.01); *H04L 63/0861* (2013.01); *G06K 2009/00939* (2013.01)

(58) Field of Classification Search
CPC ........... G06K 9/00536; G06K 9/00885; G06K 9/6269; G06N 20/10; H04L 63/0861
See application file for complete search history.

(56) References Cited

U.S. PATENT DOCUMENTS

| | | | |
|---|---|---|---|
| 8,213,664 | B2 | 7/2012 | Fyke et al. |
| 8,734,296 | B1 | 5/2014 | Brumback et al. |
| 8,924,736 | B1 | 12/2014 | Dusan et al. |
| 2001/0031602 | A1 | 10/2001 | Sagi-Dolev |
| 2014/0171196 | A1 | 6/2014 | Coyle |
| 2018/0068193 | A1* | 3/2018 | Wang .................. G06K 9/6215 |

OTHER PUBLICATIONS

Israel S A et al, "ECG to identify individuals", Pattern Recognit, Elsevier, GB, (Jan. 1, 2005), vol. 38, No. 1, doi:10.1016/J.PATCOG. 2004.05.014, ISSN 0031-3203, pp. 133-142.
ECG biometric recognition: A comparative analysis, I. Odinaka; P. Lai; A. Kaplan; J. O'Sullivan; E. Sirevaag; J. Rohrbaugh, Information Forensics and Security, IEEE Transactions on, (2012), pp. 1812-1824.
M. Vaidya, "A study of biometrics technology methods and their applications—a review", International Journal of Innovations in Engineering and Technology, (2015), vol. 5, pp. 235-240.
G. Kaur; D. Singh, "Electrocardiogram ECG as a biometric characteristic: A review", International Journal of Emerging Research in Management & Technology, (2015), vol. 4, pp. 202-206.
T. Kandgaonkar; R. Mente; A. Shinde; S. Raut, "Ear biometrics: A survey on ear image databases and techniques for ear detection and recognition", IBMRD'S Journal of Management & Research, (2015), vol. 4, pp. 88-103.
E. Ivanovas; D. Navakauskas, "Development of biometric systems for person recognition: Biometric feature systems, traits and acquisition", Elektronika Ir Elektrotechnika, (2015), vol. 101, pp. 87-90.
M. Hassan; O. Khalifa; A. Talib; A. Abdulla, "Unconstrained facial recognition systems: A review", Asian Journal of Applied Sciences, (2015), vol. 3.
A. Jain; A. Ross, "Bridging the gap: From biometrics to forensics", Philosophical Transactions of the Royal Society B, (2015), p. 2.
D. Peralta; M. Galar; I. Triguero; D. Patermain; S. Garcia; E. Barrenechea; J. Benitez; H. Bustince; F. Herrera, "A survey on fingerprint minutiae-based local matching for verification and identification: Taxonomy and experimental evaluation", Information Sciences, (2015), vol. 315, pp. 67-87.
A. Patrick, Fingerprint Concerns: Performance, Usability, and Acceptance of Fingerprint Biometric Systems, (Jun. 25, 2008), URL:http://www.andrewpatrick.ca/essays/fingerprint-concerns-performance-usability-and-acceptance-of-fingerprint-biometric-systems.
Trader, False Rejection Rate—What Does It Mean and Why Should I Care?, (Aug. 19, 2010), URL: http://blog.m2sys.com/important-biometric-terms-to-know/false-rejection-rate-%E2%80%93-what-does-it-mean-and-why-should-i-care.
Characteristics of Biometric Systems, (Jan. 11, 2016), URL:http://www.cccure.org/Documents/HISM/039-041.html.
T. Mansfield, Biometric Authentication in the Real World, (Jan. 11, 2016), URL:http://www.npl.co.uk/upload/pdf/biometrics_psrevho.pdf.
A. De Luca; A. Hang; F. Brudy; C. Lindner; H. Hussman, "Touch me once and i know it's you!: Implicit authentication based on touch screen patterns", Proceedings of the Sigchi Conference on Human Factors in Computing Systems, (2012), pp. 987-996.
S. Israel; J. Irvine; A. Cheng; M. Wiederhold; B. Wiederhold, "ECG to identify individuals", Pattern Recognition, (2005), vol. 38, pp. 133-142.
F. Gargiulo; A. Fratini; M. Sansone; C. Sansone, "Subject identification via ECG fiducial-based systems: Influence of the type of QT interval correction", Computer Methods and Programs in Biomedicine, (2015), vol. 121, p. 127.
Z. Fatemian; D. Hatzinakos, "A new ECG feature extractor for biometric recognition", Digital Signal Processing, 2009 16th International Conference on IEEE, (2009), pp. 1-6.
G. Wubbeler; M. Stavridis; D. Kreiseler; R. Bousseljot; C. Elster, "Verification of humans using the electrocardiogram", Pattern Recognition Letters, (2007), vol. 28, pp. 1172-1175.
A. Kennedy; D. Epstein; M. Jobes; D. Agage; M. Tyburski; K. Phillips; A. Ali; R. Bari; S. Hossain; K. Hovsepian, "Continuous in-the-field measurement of heart rate: Correlates of drug use, craving, stress, and mood in polydrug users", Drug and Alcohol Dependence, (2015), vol. 151, pp. 159-166.
R. Rani; V. Chounan; H. Sinha, "Automated Detection of QRS Complex in ECG Signal using Wavelet Transform", International Journal of Computer Science and Network Security, (2015), vol. 15, p. 1.
B. Kohler; C. Hennig; R. Orglmeister, "The principles of software QRS detection", Engineering in Medicine and Biology Magazine, IEEE, (2002), vol. 21, pp. 42-57.
P. Hamilton; W. Tompkins, "Quantitative investigation of QRS detection rules using the MIT/BIH arrhythmia database", Biomedical Engineering, IEEE Transactions on, (1986), vol. 12, pp. 1157-1165.
D. Clifford, "ECG statistics, noise, artifacts, and missing data", Advanced Methods and Tools for ECG Data Analysis, (2006), pp. 55-99.
Sansone M, Fusco R, Pepino A, Sansone C. Electrocardiogram pattern recognition and analysis based on artificial neural networks and support vector machines: a review. J Healthc Eng. 2013; 4(4): 465-504.
Choi H-S, Byunghan L, Sungroh Y Biometric Authentication Using Noisy Electrocardiograms Acquired by Mobile Sensors. IEEE Access 2016; 4: 1266-1273.

\* cited by examiner

BIOMETRIC METHOD AND DEVICE FOR IDENTIFYING A PERSON THROUGH AN ELECTROCARDIOGRAM (ECG) WAVEFORM

CROSS-REFERENCE TO RELATED APPLICATIONS

This application is a U.S. National Stage Application under 35 U.S.C. § 371 of International Patent Application No. PCT/IB2017/052499, filed Apr. 28, 2017, which claims priority to Portugal Application No. 109357, filed Apr. 29, 2016, which are hereby incorporated by reference in their respective entireties.

TECHNICAL FIELD

The present disclosure relates to a biometric method and device for identifying a person through electrocardiogram (ECG) morphology-derived waveform characteristics, using only one or a very few number of heartbeats.

BACKGROUND

In the past few years, more safer and trustable identity recognition methods in comparison with the conventional techniques used so far are being extensively explored. Identity recognition has applications in several facets of life, including security technology, e-commerce, data protection, entertainment, remote access, voting, health and social services [1]. However, traditional identity recognition methods, such as passwords or encryption keys, have numerous constraints. Those methods can be vulnerable and inefficient for sensing a certain physiologic change or simply for identifying a specific person. Consequently, researchers have begun investigating the possibility of using biometric measures in order to recognize a person. Currently, biometrics-based identity recognition is a rapidly growing research area not only due to the increasing demands for security in healthcare and law enforcement applications [3], but also to be applied in the development of novel and attractive systems for entertainment applications. In addition to security or other technological industries, the media and entertainment sectors have been also applying biometrics in the industry of user-adaptable objects in order to make it even more user-friendly. Indeed, human-interactive technologies are being extensively explored in order to develop smart objects and systems capable of interact with its user for a number of different applications. Recently, significant efforts were made in order to develop an apparatus able to recognize its user through biometric inputs and interact with him.

Identity authentication using one or more biometric measures ensures identification, authentication and nonrepudiation in information security [3]. Fingerprint, retina, face, iris and voice recognition were the first technologies being explored in the field of biometrics. Recently, several studies proved that it is possible to identify an individual through morphological features extracted by imaging its ear, odour, keystroke or individual gait to identify persons. However, recent findings revealed that all those methods have also several drawbacks. Despite a lot of research was done in the past years in order to develop and improve the biometric technologies cited above, much more improvements must be done in future years. For example, for an individual to be identified through face-derived features, the underlying authentication algorithm must to analyse specific characteristics such as the width of the nose, the distance between eyes, jaw line, among others. However, those features are constantly suffering from on-going changes resultant from changes in the person facial expression, which can introduce a large variability in the features set used for identity recognition and compromise classifier generalization ability. In addition, as the person gets older, his face changes by the age, contributing even more for the larger variability of face-derived features. For those reasons, near perfection accuracy results have been achieved by human facial recognition algorithms recently developed only under highly controlled environments (approximately 97.23%), being its performance highly influenced by several factors such as illumination or subject position.

Although being one of the most mature technologies, fingerprint recognition has also several drawbacks. Its potential can be fooled using a synthetic material, such as gelatine. Additionally, in some situations, such as unconstrained environments, the quality of the acquired data may be not amenable for an automated recognition, being the majority of input samples rejected by this type of algorithms. However, fingerprint recognition algorithms which ensure a near perfect performance were already developed, showing accuracy values of approximately 99%. Despite the accuracy being the measure most frequently considered for analysing the strength of biometric systems, not only this measure is important to evaluate the performance of such systems. In addition to accuracy, statistic measures such as the False Rejection Rate (FRR), False Acceptance Rate (FAR) and Speed and Throughout Rate (STR) must be also computed in order to correctly characterize a method for biometric purposes [15]. The False Rejection Rate is defined as the frequency of times when biometric information is not matched against any records in a database, when a person who is enrolled in the system tries to validate his/her identity. A biometric system associated with a high FRR can be particularly frustrating, causing unnecessary logs, affecting service and a negative impact in the productivity [16]. The FAR is the statistical measure which represents the degree at which a person is falsely reported to match the biometric template or information belonging to another person in the database [15]. Finally, the Speed and Throughout Rate reflects the method data processing capability, transducing the time for a decision (accept or reject the ID) being announced by the biometric system [17]. The relationship between FAR and FRR associated with the fingerprint recognition method reveals that this technique performs best for low acceptance rates [18], in comparison with the other methods represented in the FIG. 1. However, fingerprint recognition has a relevant drawback that significantly affect the performance of the method: its high False Rejection Rate—independently of the detection performance, the system reject about 10% of its input values. Voice, hand and face recognition have a highly variable behaviour in comparison with fingerprint—these three techniques must to reject almost all of the input samples in order to ensure performance values similar to fingerprint recognition. The iris system reveals to be the best relatively to all the techniques—with only 1.8% of false rejections. However, the complexity of this method significantly increases, in comparison with the remaining ones. Relatively to the Speed and Throughout Rate, according with a study conducted by the UK Passport Service [15], the majority of the fingerprint recognition systems have a Speed and Throughout Rate between 45 seconds and 1 minute and 45 seconds. Only in recent years, biometric systems were able to reach speed detection values between 6-10 seconds and, even today, several systems in the market do not ensure this response rapidity. Taking into account these facts, the response speed of this type of techniques remains a challenging topic in the field of biometrics.

Besides improving the performance values mentioned above associated with the existing biometric identity systems, researchers have begun to investigate novel biometric technologies for individual identification, in order to correct the drawbacks of the first ones. Recently, some researchers proposed identity recognition methods based on the individual touching behavior, by exploiting biometrical features such as position, pressure or size, when a subject simply inputs a pattern password into a touch screen. However, this novel method has also implications that compromise its performance. The fact that it is only focused on the collection of pattern data provided from a single type of sensor and taking into account that an individual can hold/touch a certain object by different manners in different occasions, enhances its feasibility. Therefore, scientists made efforts in order to develop a system able to recognize its user through the information provided from a more robust biometric signature, that could not be affected by sudden and significant changes observed in the emotional state, age, acquisition local, subject position, between other factors. For the reasons detailed above, the application of electrocardiography (ECG) for biometric purposes has been studied in the past few years [3]. It has been established that this type of biological signal, besides providing liveliness detection, is strongly correlated to the subject arousal level [3]. Additionally, the ECG signal is hard to steal and impossible to mimic, because it is unique and intrinsic to each subject. ECG describes the electrical activity of the heart, providing information about the heart rate, rhythm and morphology [21]. A typical ECG wave provided from a healthy subject is composed by the fiducial points: P, Q, R, S and T (a P wave, a QRS complex and a T wave)—see FIG. 2—[21] [22].

Physiological and geometrical differences, such as differences in heart position, size, conductivity of various cardiac muscles, cardiac activation order and physical conditions are the main physiological factors for the heterogeneity of ECG signals among individuals.

Recently, researchers has classified ECG-based biometric techniques in two types: the ones that are based in the fiducial points detection, and the ones based on the extraction of features in frequency domain. The first type of biometric techniques suppose direct time domain feature extraction, being the first method for ECG-based biometric reported in the literature [21]. The features used in this type of classification are only based in the morphology of the ECG, being of simple extraction. They are mostly based on the location of ECG fiducial points (P, Q, R, S, T). Some examples of this type of features are P wave duration, P amplitude, QRS duration, QRS amplitude, T duration, T amplitude—temporal intervals and amplitude difference between fiducial points. Currently, most of those time-domain features are mostly used for cardiovascular diagnosis [21]. Recent research studies proved that there are some characteristics of the ECG waveform, regarding wave shape, amplitude, temporal interval between fiducial points, which could be permanent, distinctive from person to person and stable enough to correctly identify a subject [22].

One of the problems of the ECG-based biometric systems which use time-domain features is the time varying nature of ECG waves. Indeed, the morphology of the ECG signal acquired even for few seconds can vary from time to time even for the same subject [21], due to sudden changes on the cardiac heart rate, which is controlled by the autonomic nervous system (ANS) [22]. Time intervals among fiducials points change with varying heart rate [22] [23], and it is being a challenge to find a suitable normalization method to avoid high misclassification rates associated with the time variability of the heart rate. Currently, the majority of the ECG-based identity recognition algorithms developed so far are included in the second type, the ones that use frequency-derived features and wavelet-based measures, being therefore computationally demanding and time consuming, requiring highly complex hardware architectures [23] [24]. However, those algorithms are even much more computationally demanding in comparison with the ones that use only frequency-derived features.

In a world where the small-scale technology has been extremely valued, where mobile and wearable technology are emerging as the next big market, most of all with applications in the industry of entertainment and gaming, more simpler biometric algorithms are required to cope with processing and storage limitations. Recently, several small-scale interactive systems designed to be controlled by biometric inputs were developed, since user-adaptable toys [25], biofeedback systems [9], video games based on brain computer interfaces (BCI) [26], etc. More efficient, simpler and faster biometric techniques are thus very important. Efforts are being made in order to develop an ECG based-algorithm for biometric purposes capable to recognize a person as briefly as possible [1]. However, not only the misclassification rate and accuracy are currently used as criteria for assessing biometric algorithms performance. Other parameters such as computational requirements (in terms of cost and time) are being broadly used for judging identification methods, being the computational cost (e.g. number and type of mathematical operations) one of the major factors that determines the acceptability of a given biometric system [21]. Recently, Wubbeler et al. [27] have proposed an algorithm which ensures classification error rates smaller than 3% using the information extracted from 10 heartbeats.

However, their method is based on ECG acquisitions from more than one-lead and only one temporal distance measure, being, therefore, vulnerable to error. Can Ye et al. [28] have also developed a method which ensures a correct subject identification using only ECG acquisitions with 6 seconds (approximately 6-8 heartbeats). However, it applies features extraction methods and uses 26 features for training the classifier, implying a high computational cost. To our knowledge, no other work has proposed a method capable of identifying a person using less heartbeats.

These facts are disclosed in order to illustrate the technical problem addressed by the present disclosure.

REFERENCES

[1] I. Odinaka, P. Lai, A. Kaplan, J. O'Sullivan, E. Sirevaag and J. Rohrbaugh, "ECG biometric recognition: A comparative analysis," Information Forensics and Security, IEEE Transactions on, pp. 1812-1824, 2012.

[2] M. Vaidya, "A study of biometrics technology methods and their applications—a review," International Journal of Innovations in Engineering and Technology, vol. 5, pp. 235-240, 2015.

[3] G. Kaur, D. Singh and S. Kaur, "Electrocardiogram ECG as a biometric characteristic: A review," International Journal of Emerging Research in Management & Technology, vol. 4, p. 202-206, 2015.

[4] D. Benyon, P. Turner and S. Turner, Designing interactive systems: People, activities, contexts, technologies, Pearson Education, 2005.

[5] L. Nacke, A. Drachen, K. Kuikkaniemi, J. Niesenhaus, H. Korhonen, V. Hoogen, K. Poets, W. IJsselsteijn and Y. Kort, Playability and player experience research, Proceedings of DiGRA, 2009.

[6] S. Fyke, N. Ladouceur and J. Griffin, "Shape-adaptable surface for an audio port". U.S. Pat. No. 8,213,664, 2012.

[7] L. Lenkarski and J. DeCarolis, "Base frame for game using an electric probe in adaptable configurations". U.S. Pat. No. 7,988,561, 2011.

[8] J. Baier, D. Wylie, D. Vasko and D. Callaghan, "System and methodology providing adaptive interface in an industrial controller environment". U.S. Pat. No. 8,132,127, 2012.

[9] C. Brumback, D. Knight, J. Messenger and J. Hong, "Biometric sensing device having adaptive data threshold, a performance goal, and a goal celebration display". U.S. Pat. No. 8,734,296, 2014.

[10] T. Kandgaonkar, R. Mente, A. Shinde and S. Raut, "Ear biometrics: A survey on ear image databases and techniques for ear detection and recognition," IBMRD's Journal of Management & Research, vol. 4, p. 88-103, 2015.

[11] E. Ivanovas and D. Navakauskas, "Development of biometric systems for person recognition: Biometric feature systems, traits and acquisition," Elektronika it Elektrotechnika, vol. 101, p. 87-90, 2015.

[12] M. Hassan, O. Khalifa, A. Talib and A. Abdulla, "Unconstrained facial recognition systems: A review," Asian Journal of Applied Sciences, vol. 3, 2015.

[13] A. Jain and A. Ross, "Bridging the gap: From biometrics to forensics," Philosophical Transactions of The Royal Society B, p. 2, 2015.

[14] D. Peralta, M. Galar, I. Triguero, D. Patermain, S. Garcia, E. Barrenechea, J. Benitez, H. Bustince and F. Herrera, "A survey on fingerprint minutiae-based local matching for verification and identification: Taxonomy and experimental evaluation," Information Sciences, vol. 315, p. 67-87, 2015.

[15] A. Patrick, "Fingerprint Concerns: Performance, Usability, and Acceptance of Fingerprint Biometric Systems," 25 Jun. 2008. [Online]. Available: http://www.andrewpatrick.ca/essays/fingerprint-concerns-performance-usability-and-acceptance-of-fingerprint-biometric-systems/. [Accessed 11 Jan. 2016].

[16] J. Trader, "False Rejection Rate—What Does It Mean And Why Should I Care?," 19 Aug. 2010. [Online]. Available: http://blog.m2sys.com/important-biometric-terms-to-know/false-rejection-rate-% E2%80%93-what-does-it-mean-and-why-should-i-care/. [Accessed 11 Jan. 2016].

[17] "Characteristics of Biometric Systems," [Online]. Available: https://www.cccure.org/Documents/HISM/039-041.html. [Accessed 11 Jan. 2016].

[18] T. Mansfield, "Biometric authentication in the real world," [Online]. Available: http://www.npl.co.uk/upload/pdf/biometrics_psrevho.pdf. [Accessed 11 Jan. 2016].

[19] Y. Liu, J. Liu, Z. Lin, X. Luo and J. Duan, "I know it's you: Touch behavioral characteristics recognition on smartphone based on pattern password," in Pacific Asia Conference on Information Systems, 2015.

[20] A. De Luca, A. Hang, F. Brudy, C. Lindner and H. Hussman, "Touch me once and i know it's you!: Implicit authentication based on touch screen patterns," in Proceedings of the SIGCHI Conference on Human Factors in Computing Systems, 987-996, 2012.

[21] F. Sufi, I. Khalil and J. Hu, ECG-based authentication, Handbook of Information and Communication Security: Springer Berlin Heidelberg, 2010.

[22] S. Israel, J. Irvine, A. Cheng, M. Wiederhold and B. Wiederhold, "ECG to identify individuals," Pattern recognition, vol. 38, p. 133-142, 2005.

[23] F. Gargiulo, A. Fratini, M. Sansone and C. Sansone, "Subject identification via ECG fiducial-based systems: Influence of the type of QT interval correction," Computer Methods and Programs in Biomedicine, vol. 121, p. 127, 2015.

[24] Z. Fatemian and D. Hatzinakos, "A new ECG feature extractor for biometric recognition," Digital Signal Processing, 2009 16th International Conference on IEEE, p. 1-6, 2009.

[25] A. Sagi-Dolev, "Interactive interface for infant activated toys". Patent US20010031602, 2001.

[26] D. Coyle, "Control panel". Patent US20140171196, 2014.

[27] G. Wubbeler, M. Stavridis, D. Kreiseler, R. Bousseljot and C. Elster, "Verification of humans using the electrocardiogram," Pattern Recognition Letters, vol. 28, p. 1172-1175, 2007.

[28] C. Ye, V. Kumar and M. Coimbra, "Human identification based on ECG signals from wearable health monitoring devices," in Proceedings of the 4th International Symposium on Applied Sciences in Biomedical and Communication Technologies 2011, 2011.

[29] J. Pan and W. Tompkins, "A real-time QRS detection algorithm," Biomedical Engineering, IEEE Transactions on, 1985.

[30] A. Kennedy, D. Epstein, M. Jobes, D. Agage, M. Tyburski, K. Phillips, A. Ali, R. Bari, S. Hossain, K. Hovsepian, M. Rahman, E. Ertin, S. Kumar and K. Preston, "Continuous in-the-field measurement of heart rate: Correlates of drug use, craving, stress, and mood in polydrug users," Drug and Alcohol Dependence, vol. 151, p. 159-166, 2015.

[31] R. Rani, V. Chounan and H. Sinha, "Automated Detection of QRS Complex in ECG Signal using Wavelet Transform," International Journal of Computer Science and Network Security, vol. 15, p. 1, 2015.

[32] B. Kohler, C. Hennig and R. Orglmeister, "The principles of software QRS detection," Engineering in Medicine and Biology Magazine, IEEE, vol. 21, p. 42-57, 2002.

[33] P. Hamilton and W. Tompkins, "Quantitative investigation of QRS detection rules using the MIT/BIH arrhythmia database," Biomedical Engineering, IEEE Transactions on, vol. 12, p. 1157-1165, 1986.

[34] D. Clifford, "ECG statistics, noise, artifacts, and missing data," Advanced Methods and Tools for ECG Data Analysis, p. 55-99, 2006.

SUMMARY

This disclosure includes a low computational cost method that is able to quickly identify a person through electrocardiogram (ECG) morphology-derived characteristics, using one or, in some situations, a very few number of waveform heartbeats. This method is able to achieve recognition accuracy values near 100% with low false rejection rate (FRR), which is one of the main problems of the current widespread systems. It is based on fast ECG signal processing steps—such as filters and signal derivatives—, being mostly independent of the type of classifier selected for the pattern recognition task. It ensures high performance results, according to an embodiment, by using either an Artificial Neural Network or Support Vector Machines (SVM). Resulting identity check systems can be easily embedded in small-scale devices, according to an embodiment, with simple low-cost and low-power hardware. They can be applied to several domains, such as user interaction, entertainment and gaming (user-adaptable toys, human-interactive systems, etc.), security purposes (e-commerce, data protection, remote access, e-banking services, clinical validation data, etc.), among others.

In this disclosure, it is proposed a device and a method for identifying a person, by using features only based on three distance measures among ECG fiducial points on the time domain. By capturing an ECG wave for few seconds and therefore extracting the temporal distances between the Q, R, S and T fiducial points and using machine learning techniques, this method is capable to automatically identify a person using only the information provided for a single heartbeat. A great advantage of this method is its ability to recognize a specific person in real-time. An embodiment includes an advantageous normalization step. In order to compensate the sudden changes in individual heart rate, according to an embodiment, new heartbeat-derived features are normalized using the average RR distance across all subjects calculated using the training set. Using this step, features provided from a new heartbeat can be therefore normalized and projected in the training features space independently from the current individual heart rate, being possibly to recognize the person whose heartbeat belongs to. The disclosure may be also used for other applications, such as healthcare and security purposes.

It is disclosed a method for identifying a person through an electrocardiogram, ECG, waveform, said method comprising:
  capturing ECG signals from a sample population including the person to be identified;
  computing ECG fiducial points Q, R, S and T of the sample population from the captured ECG signals;
  computing the ECG distances consisting of ECG distances ST, RT and QT, or any other three linear-combination distances of ST, RT and QT, from the computed ECG fiducial points Q, R, S and T of the sample population;
  training a computer classification model on the computed sample population ECG distances;
  capturing an ECG signal from the person to be identified;
  computing the person's ECG fiducial points Q, R, S and T from the person's captured ECG signal;
  computing the ECG distances consisting of ECG distances ST, RT and QT, or the same three linear-combination distances of ST, RT and QT used when training the computer classification model, from the person's computed ECG fiducial points Q, R, S and T;
  using the classification model with the person's computed ECG distances to identify the person to be identified within the sample population.

It is disclosed a method for identifying a person through an electrocardiogram, ECG, waveform, against a previously trained computer classification model using a sample population including the person to be identified, said method comprising:
  capturing an ECG signal from the person to be identified;
  computing the person's ECG fiducial points Q, R, S and T from the person's captured ECG signal;
  computing the ECG distances consisting of ECG distances ST, RT and QT, or three linear-combination distances of ST, RT and QT previously used when training said computer classification model, from the person's computed ECG fiducial points Q, R, S and T;
  using the classification model with the person's computed ECG distances to identify the person to be identified within the sample population;
  wherein the classification model was previously trained on sample population ECG distances consisting of ECG distances ST, RT and QT, or any other three linear-combination distances of ST, RT and QT, which were computed from the computed ECG fiducial points Q, R, S and T which were computed from captured ECG signals from the sample population.

An embodiment comprises normalizing the computed ECG distances ST, RT and QT, of the sample population and of the person to be identified, using an average of the ECG distance RR computed from the captured ECG signals from the sample population.

An embodiment comprises computing ECG distances from the captured ECG signals of the sample population for up to a maximum of 25 to 60 heartbeat waveforms for each population member, in particular up to a maximum of 35 to 50 heartbeat waveforms for each population member, or between 25 and 50 heartbeats for each population member, or between 35 to 60 heartbeats for each population member.

An embodiment comprises computing ECG distances from the captured ECG signals of the person to be identified for 1 to 2 heartbeat waveforms.

In an embodiment, computing the ECG distances ST, RT and QT of a heartbeat waveform includes:
  determining the fiducial points Q, R, S and T from the heartbeat waveform, and
  calculating the time intervals between S and T for ECG distance ST, between R and T for ECG distance RT, and between Q and T for for ECG distance QT.

In an embodiment, computing the ECG distance RR of a heartbeat waveform includes:
  determining the fiducial point R from the heartbeat waveform and the fiducial point R from the preceding heartbeat waveform, and
  calculating the time interval between the two fiducial points R for ECG distance RR.

An embodiment comprises rejecting the computed ECG distances of a heartbeat waveform if the heartbeat waveform is determined to be a noisy waveform.

In an embodiment, a heartbeat waveform is determined to be a noisy waveform if the following formula is verified:

$$QR \leq 0.075 \text{ s and } 0.200 \text{ s} < \frac{QT}{\sqrt{RR}} < 0.360 \text{ s}.$$

In an embodiment, computing the ECG distances QR, QT and RR of a heartbeat waveform includes:
  determining the fiducial points Q, R and T from the heartbeat waveform,
  calculating the time intervals between Q and R for ECG distance QR, between Q and T for ECG distance QT,
  determining the fiducial point R from the preceding heartbeat waveform, and
  calculating the time interval between the two fiducial points R for ECG distance RR.

An embodiment comprises filtering the captured ECG signal.

An embodiment comprises capturing the ECG signal from the person to be identified for a plurality of heartbeats, performing said method according to any of the described method embodiments for identifying a person, for each captured heartbeat, and selecting the person that was identified more frequently over said plurality of heartbeats.

It is also disclosed a non-transitory storage media including program instructions for implementing a method for identifying a person through an electrocardiogram, ECG, waveform, the program instructions including instructions executable to carry out the method of any of the described embodiments.

It is also disclosed a device for identifying a person through an electrocardiogram, ECG, waveform, said device comprising a non-transitory storage media according to the previously described.

It is also disclosed a device comprising an ECG capture circuit and a digital data processor for carrying out said program instructions.

It is also disclosed a device comprising an ECG capture circuit and a digital data processor arranged to carry out the method of any of the described embodiments.

BRIEF DESCRIPTION OF THE DRAWINGS

The following figures provide preferred embodiments for illustrating the description and should not be seen as limiting the scope of invention.

DETAILED DESCRIPTION

The method preferably comprises several main steps from the raw ECG signal till subject identification label: ECG processing, feature creation, feature processing, classifier training and test. It is to be noted that, in the present disclosure, each class equates to each label, and that each class and each label equate to each individual to be identified.

The following pertains the ECG processing for the location of fiducial points. At first, the method is comprised of a sequence of processing steps—step (1) in the FIG. 3—in order to remove noise artefacts and clean the ECG signal, for fiducial points be quickly, easily and correctly marked—step (2) of the FIG. 3 —, preferably using only threshold conditions. In general, Independently of the type of features extracted, an ECG signal with a high percentage of noise could lead to errors in the classifier training phase and high misclassification rates. As was referred before, the majority of ECG-based processing schemes includes computationally demanding mathematical operations, such as averaging, filtering, wavelet decomposition, among others. In this particular step, fiducial points are located on the raw signal in order to compute the three temporal distances between fiducials Q, R, S, and T used for identifying the user—distances ST, RT and QT. Note that similar classification accuracy values could be obtained with any other three linear combinations equivalent to ST, RT and QT segments (e.g. similar accuracy values will be obtained if distances QR, RS and ST were used instead of ST, RT and QT).

Figure 4:
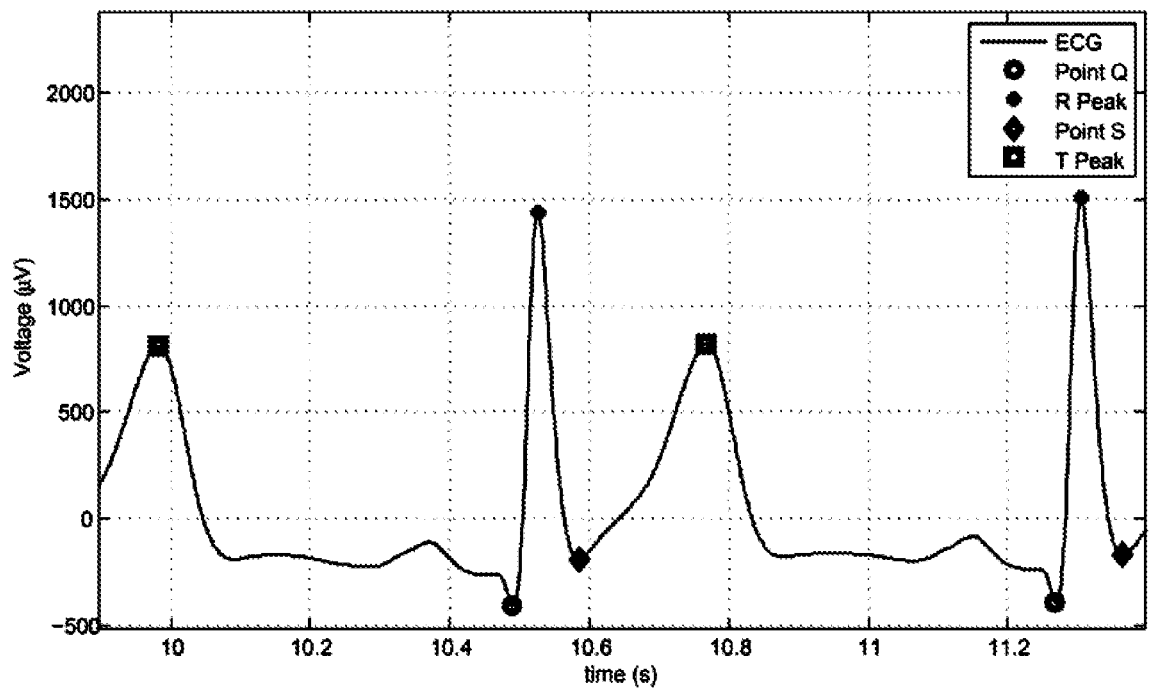
FIG. 4: Portion of ECG signal (one heartbeat) processed using the method described above. Identification of fiducial points Q, R S and T.

According to an embodiment, the R points may be located using the Pan Tompkins algorithm [29], which has been extensively used for the last 2 decades in the majority of the studies related with ECG waveform [30] [31] [32] [33], these references being hereby included in their totality. Therefore, in order to identify the remaining points (Q, S and T), the raw signal may be filtered using a Butterworth low-pass filter with a cut off frequency of 10 Hz—adequate for the ECG sampling rate. The Q points may be identified by computing the signal derivative considering a time window of 0.04 seconds defined before each R point. The last temporal mark (and the closest one relatively to each R complex) at which the derivative signal crosses zero considering this time window may be marked as point Q for each heartbeat. A similar method may be used for locating the point S. The first temporal mark at which the derivative changes from negative to positive values, in a time window between 2 milliseconds and 0.10 seconds defined after each point R, is assigned as the point S. For locating the T wave, it may be determined the last temporal index where the derivative of the signal changes from positive to negative values, considering a time window between 0.10 and 0.38 seconds after each R complex. The time windows considered to discover each fiducial point may be defined based on previously established physiological limits [34]. See FIG. 4 for an illustration of the fiducials marked according with the locations given by the presently disclosed method.

The following pertains to the feature creation. After locating fiducial points, the temporal distances between the fiducial points (Q, R, S and T) are computed for each heartbeat, in order to be used as features for the classification task—step (3) of the FIG. 3. Therefore, in order to reject the feature vectors corresponding to noisy heartbeats, the indexes of heart segments which do not satisfy the following conditions can be removed—step (4) of the FIG. 3:

$$QR \leq 0.075 \text{ s and } 0.200 \text{ s} < \frac{QT}{\sqrt{RR}} < 0.360 \text{ s}.$$

The features used in the decision function in the pattern recognition task are based on the temporal distance between the fiducial points Q, R, S and T. Three features are considered by this method: the time interval between Q and T (QT); between R and T (RT) and S and T (ST).

Figure 5:
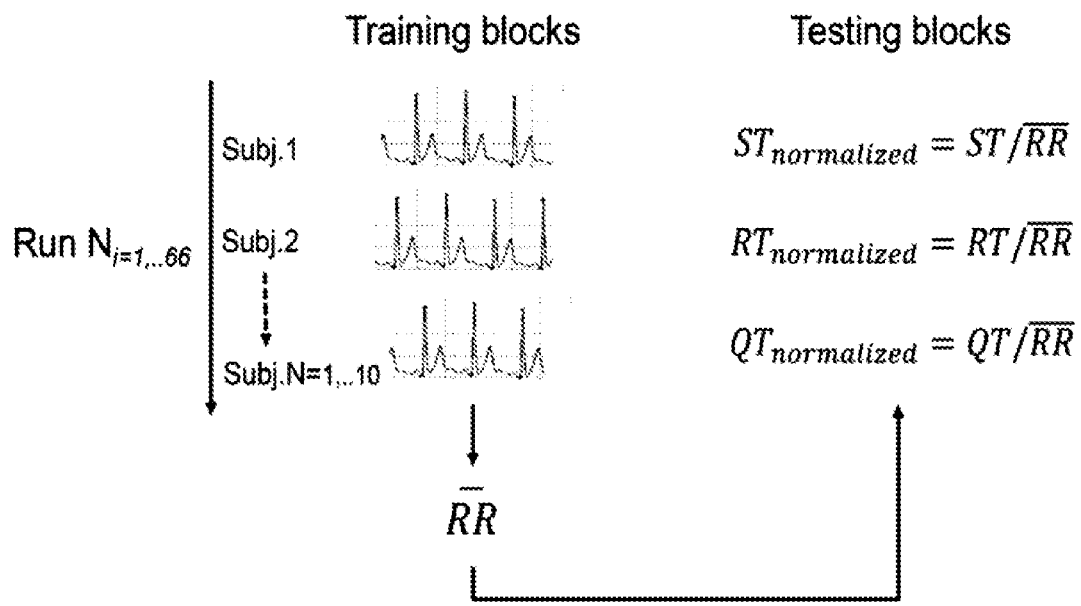
FIG. 5: Schematic representation of an embodiment of the features normalization procedure, based on the average temporal distance between consecutive R peaks across subjects.

The following pertains to the pattern recognition. After computing the features used in the pattern recognition task and in order to perform a classification independently of the subject heart rate, the three features—both training and test distances ST, RT and QT—may be normalized using the average RR distance (RR) across all subjects in the training set. Using this physiology-based step, features provided from a new heartbeat can be therefore normalized and projected in the training features space independently from the current individual heart rate, leading a correct identification of the current user—steps (5) and (7) of FIG. 3; and FIG. 5.

The following pertains to the training of the classification method for the pattern recognition. After computing feature vectors, it is needed to choose the classification method—for example Support Vector Machines, K-Nearest Neighbour classifier or Neural Networks. Therefore, the dataset used can be partitioned in three subsets: one for training the classifier, other for classification validation—in order to select the most adequate classifier parameters (step (6) of the FIG. 3)—and; at last, one subset for testing the classifier chosen—for computing classifier performance.

The following pertains to the testing of the classification method for the pattern recognition. After determining the parameter values more suitable for the classifier selected using the validation set, accuracy measures may be computed using a data subset not involved in the training. If the dataset used in the pattern recognition problem is not balanced relatively to the number of samples per class (e.g. number of heartbeats per subject), the most adequate performance measure in terms of the rate of heartbeats correctly assigned to a subject, is normally the F-Measure—which reflects both the sensibility and sensitivity of a method. If a significant difference is not observed between the number of heartbeats per individual, performance rate can be evaluated simply using the accuracy.

Figure 1:
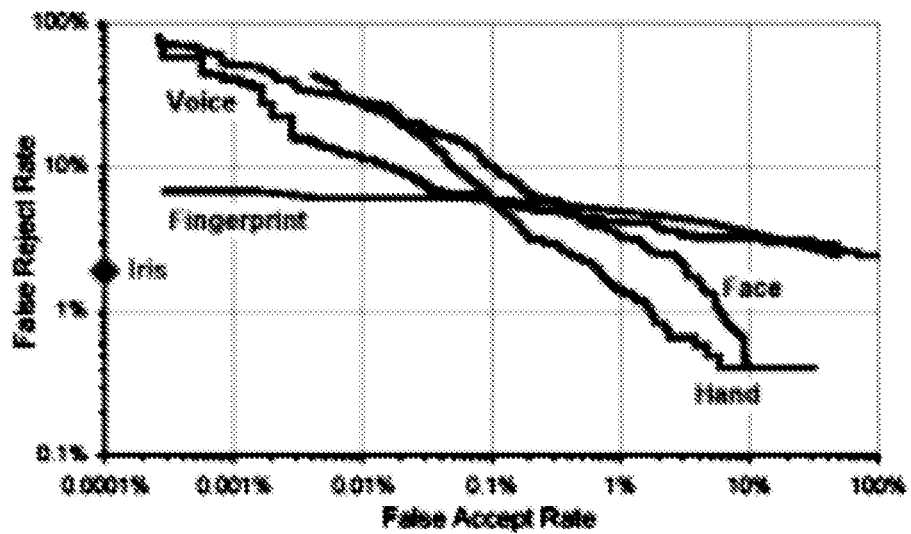
FIG. 1: Schematic representation of FAR versus FRR curve for several state-of-the-art biometric techniques [18].
Figure 2:
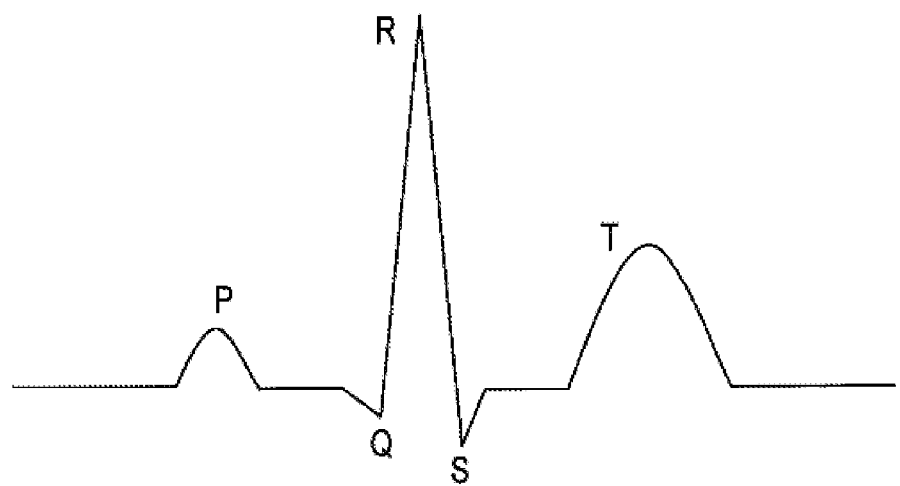
FIG. 2: Schematic representation of an heartbeat waveform with ECG fiducial points P, Q, R S and T.
Figure 3:
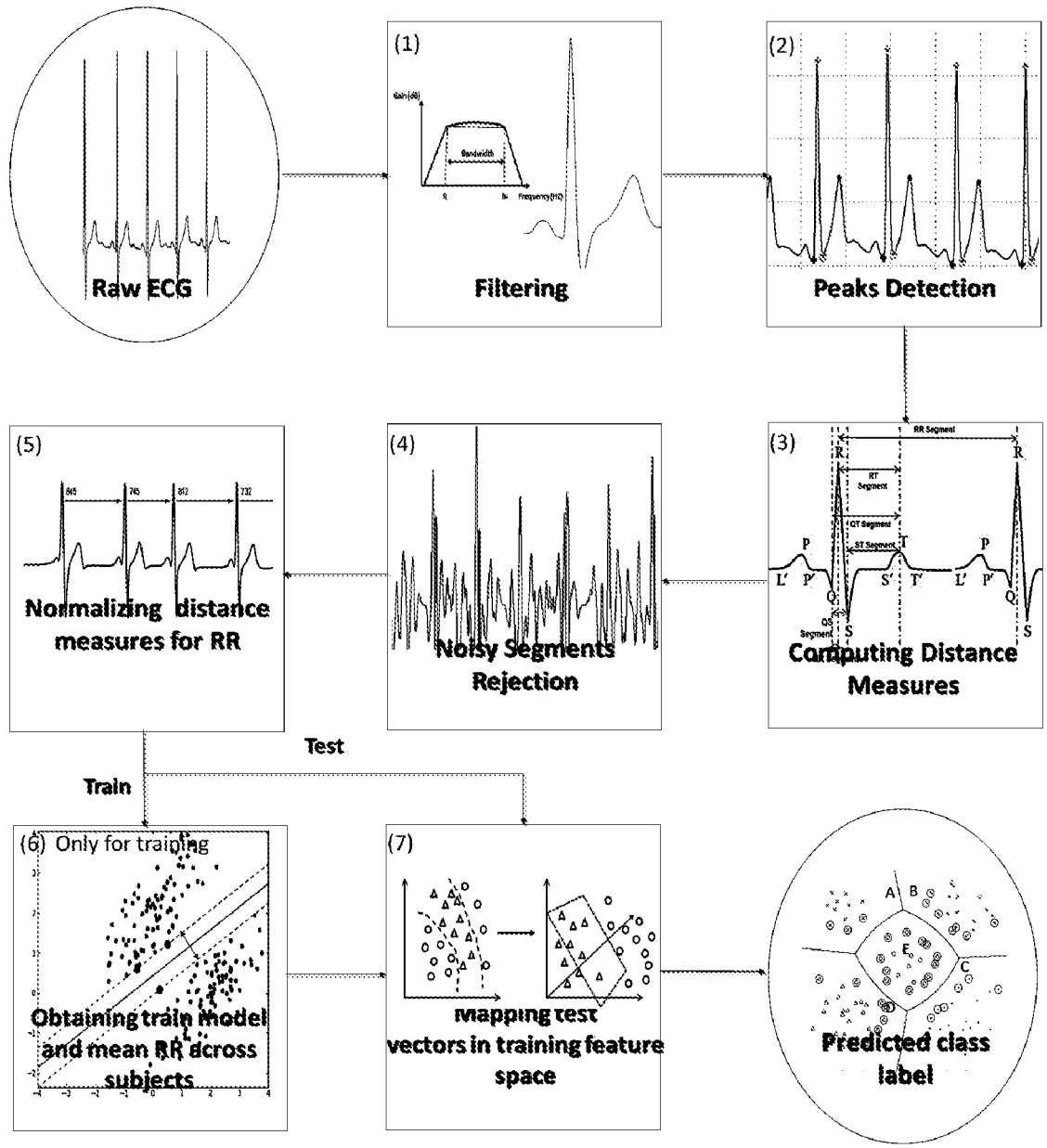
FIG. 3: Schematic representation of an embodiment of the described method steps. At first, the raw signal is filtered (1) and, then, fiducial points are located (2). After that, the distance measures are computed (3) and the noisy heartbeats are removed (4). Considering the training phase, distance measures are therefore normalized according to subject's heart rate (5). Training features are used to optimize SVM classifier settings and to build the best training model (6). In the test phase, after obtaining the processed data, test vectors are mapped into the training feature space using the model build in the train and average train RR across subjects for obtaining the predicted label (7).

Both the classification model build with the most adequate parameters set determined in the validation task, and the averaged RR value across samples and subjects computed in the training dataset—step (6) and (7) of the FIG. 3 —, are used to classify each new instance (e.g. heartbeat).

Figure 6:
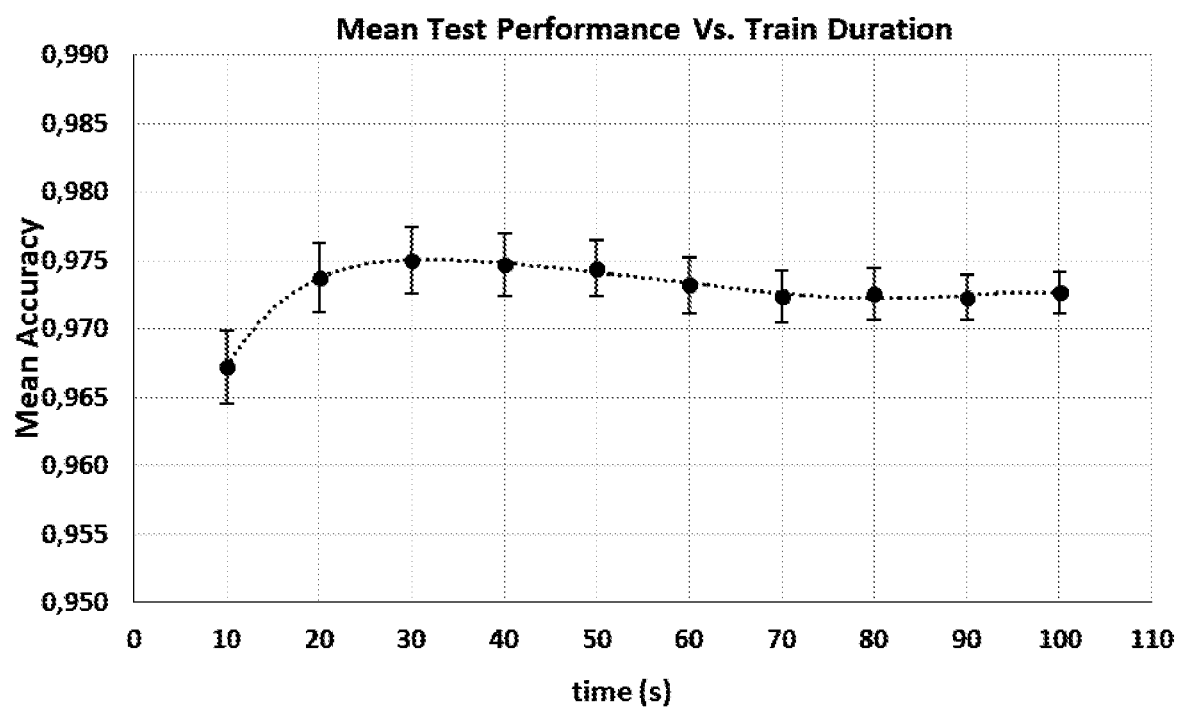
FIG. 6: Schematic representation of the mean test accuracy obtained for a 10-subjects group across 66 different combinations between train and test sets, for several values of train duration; and corresponding standard error bars.

The following pertains to the results obtained, in particular to the robustness of the device and method (Accuracy, FAR, FRR and Speed and Throughout Rate) for the classification accuracy on a 10-subjects group. In the FIG. 6 is presented a graph that shows the results obtained using the method described above (using the Support Vector Machines as classifier in the pattern recognition task), for a group of 10 subjects. In the graph is presented the evolution of the accuracy with the training time. The averaged accuracy results plotted in the graph were obtained by applying the method proposed above for 66 different combination between different train and test sets. The dataset used here was balanced relatively to the number of samples per individual.

In general, the method proposed ensures mean accuracy values above 96%, reaching a maximal value of 97.5% (near 100%) for a training duration between 30 and 40 seconds (approximately 25-50 heartbeats), being unnecessary to train the classifier for more time, given that the classifier performance stabilizes for longer training durations.

Figure 7:
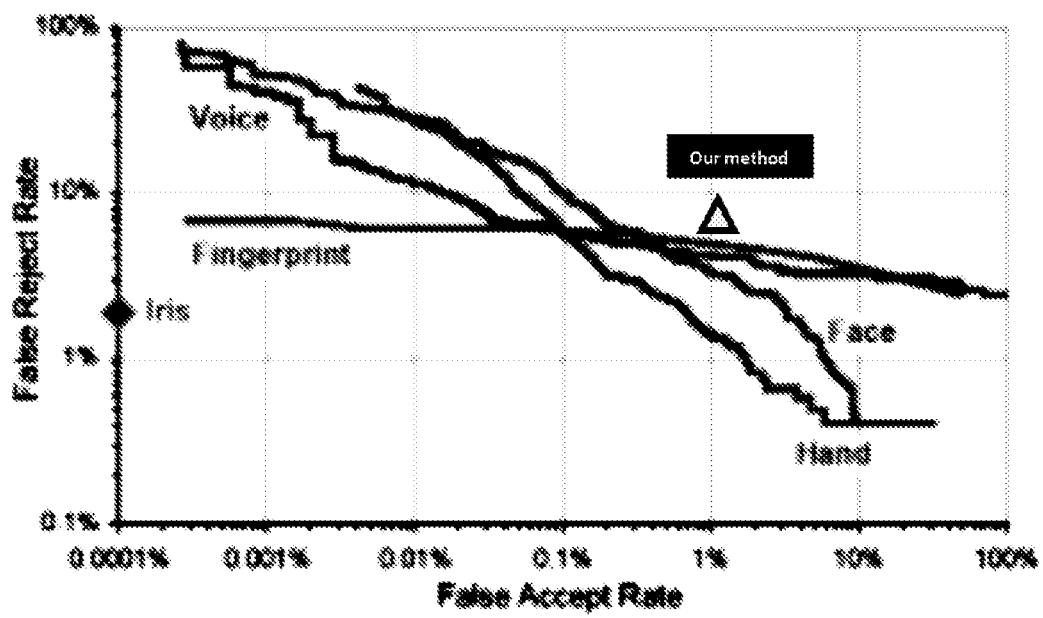
FIG. 7: Schematic representation of FAR versus FRR curves for several techniques in comparison with the presently disclosed method (represented by the triangle). Adapted from [18].

By running the method for 66 different combination between train and test sets, it was possible to plot the mean FAR and corresponding average FRR in the graphic that illustrates the relation between FAR and FRR, and comparing with the performance curves of the other techniques (FIG. 7). We obtained an average value for the FAR and FRR of 5.71±1.9% and 3.44±1.98%, respectively. Those results demonstrate that, unlike voice, face and hand recognition, the disclosed method ensures both FAR and FRR within a narrow range of values, demonstrating a consistent performance behaviour. Note that our method ensures similar False Acceptance Rate values in comparison with the fingerprint verification—the technique considered the most mature nowadays —, by rejecting less input samples, and being much less complex and costly.

In the next figure (FIG. 8) is presented the average values of the number of heartbeats necessary to identify each subject across 1000 times repetition and along 66 combinations between different train and test sets (note that for each combination, the test set used was never involved in the training), for each training duration.

Figure 8:
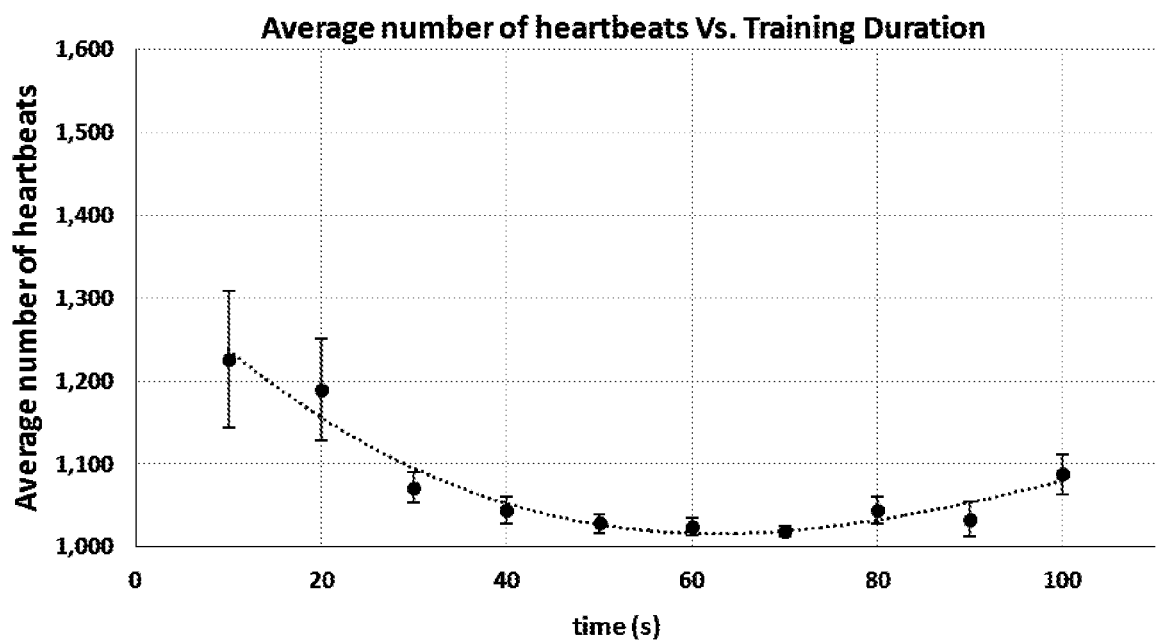
FIG. 8: Schematic representation of the number of heartbeats averaged across the ten subjects and 1000 runs necessary to identify each subject individually and corresponding fit line.

We can observe from FIG. 8 that, independently of the training duration, the average number of heartbeats necessary for correctly identifying a subject is between 1 and 2, ensuring a very quick recognition of the user. Note that, if the acquisition test is composed by a given number of heartbeats, a label corresponding to an individual will be assigned to each one of the heartbeats of the acquisition test set, and each acquisition test set will be classified as belonging to the most frequently observable individual label. Using a train set with approximately 40-50 seconds (approximately 35-60 heartbeats) we can identify a subject of this 10-person group using, at average, 1.02 heartbeats.

We can therefore conclude that the Speed and Throughout Rate of this method is between 0.75 seconds and 3 seconds, being, in general, better than the methods developed so far.

The following pertains to the robustness of the method and its classification accuracy for a 15-subjects group. Therefore, as discussed, we analysed the method accuracy for a higher number of persons (for a group of 15 subjects).

In the table below is presented the results obtained with the method described above for a different group (than the referred in the previous topic) of 15 persons. The results obtained show that, even for a group of more subjects, accuracy values remain between 96% and 100%.

TABLE III accuracy per individual for a 15-person group.

| Subject | Accuracy per Subject (%) |
| --- | --- |
| Subject 1 | 100 |
| Subject 2 | 100 |
| Subject 3 | 96.10 |
| Subject 4 | 99.29 |
| Subject 5 | 98.23 |
| Subject 6 | 98.94 |
| Subject 7 | 100 |
| Subject 8 | 98.23 |
| Subject 9 | 100 |
| Subject 10 | 98.22 |
| Subject 11 | 100 |
| Subject 12 | 100 |
| Subject 13 | 97.87 |
| Subject 14 | 100 |
| Subject 15 | 100 |
| MEAN | 99.13 |

The following pertains testing the importance of the physiology-based "normalization". In order to verify if the "normalized step" proposed here (that implies the normalization of the distance measures collected for each test sample, using the mean value of RR across heartbeats and along subjects calculated in the train) significantly improves performance accuracy, in comparison with any other constant value, we evaluated accuracy values for the next 6 conditions:

I. Normalization of test samples using the physiology-based normalization proposed here;

II. Normalization of test samples using the constant value RR=0.5;

III. Classification of the test samples without normalizing them;

IV. Normalization of test samples using the constant value RR=4.0;

V. Normalization of test samples using the constant value RR=0.04;

VI. Normalization of test samples using the constant value of RR=1.6e-04.

Statistical tests were performed between the condition I and the other conditions in order to conclude if the first condition was the best option.

TABLE IV

Accuracy values per individual for each one of the conditions evaluated.

| Condition | Subject | Accuracy per Subject (%) |
|---|---|---|
| I - Normalization of test samples using the physiology-based normalizationon RR average | Subject 1 | 100 |
| | Subject 2 | 100 |
| | Subject 3 | 97.20 |
| | Subject 4 | 97.70 |
| | Subject 5 | 90.40 |
| | Subject 6 | 98.90 |
| | Subject 7 | 99.40 |
| | Subject 8 | 97.70 |
| | Subject 9 | 100 |
| | Subject 10 | 86.40 |
| | MEAN | 96.80 |
| II - Normalization of test samples using the constant value RR = 0.5 | Subject 1 | 100 |
| | Subject 2 | 100 |
| | Subject 3 | 97.20 |
| | Subject 4 | 100 |
| | Subject 5 | 96.00 |
| | Subject 6 | 99.40 |
| | Subject 7 | 99.40 |
| | Subject 8 | 97.70 |
| | Subject 9 | 100 |
| | Subject 10 | 98.90 |
| | MEAN | 98.90 |
| III - Classification of the test samples without normalizing them | Subject 1 | 100 |
| | Subject 2 | 100 |
| | Subject 3 | 95.50 |
| | Subject 4 | 97.70 |
| | Subject 5 | 87.00 |
| | Subject 6 | 98.90 |
| | Subject 7 | 99.40 |
| | Subject 8 | 97.70 |
| | Subject 9 | 100 |
| | Subject 10 | 84.2 |
| | MEAN | 96.00 |
| IV - Normalization of test samples using the constant value RR = 4.0 | Subject 1 | 100 |
| | Subject 2 | 100 |
| | Subject 3 | 87.60 |
| | Subject 4 | 89.80 |
| | Subject 5 | 92.70 |
| | Subject 6 | 88.10 |
| | Subject 7 | 96.00 |
| | Subject 8 | 91.50 |
| | Subject 9 | 100 |
| | Subject 10 | 87.60 |
| | MEAN | 96.00 |
| V - Normalization of test samples using the constant value RR = 4.0 | Subject 1 | 100 |
| | Subject 2 | 100 |
| | Subject 3 | 97.70 |
| | Subject 4 | 98.90 |
| | Subject 5 | 95.50 |
| | Subject 6 | 100 |
| | Subject 7 | 99.4 |
| | Subject 8 | 97.70 |
| | Subject 9 | 100 |
| | Subject 10 | 98.30 |
| | MEAN | 98.80 |
| VI - Normalization of test samples using the constant value of RR = 1.6e−04 | Subject 1 | 92.10 |
| | Subject 2 | 92.10 |
| | Subject 3 | 87.60 |
| | Subject 4 | 89.80 |
| | Subject 5 | 92.70 |
| | Subject 6 | 88.10 |
| | Subject 7 | 87.60 |
| | Subject 8 | 91.50 |
| | Subject 9 | 91.00 |
| | Subject 10 | 87.60 |
| | MEAN | 90.00 |

TABLE V

Results of the statistical tests performed for determining the best condition. Statistical Results - 2 sample t-test (considering accuracy values per class)

| Condition I vs. II | Condition I vs. III | Condition I vs. IV | Condition I vs. V | Condition I vs. VI |
|---|---|---|---|---|
| p = 0.138 | p = 0.096 | p = 0.04 | p = 0.135 | p = 0.002 |

Taking into account the results obtained in the statistical tests, the value of the constant used for normalizing new test samples really matters. Indeed, a significant difference was found between condition I and IV, and between condition I and VI. Considering that the value of the averaged accuracy along subjects is higher in condition I relatively to both the conditions IV and VI, the use of the training mean RR across all heartbeats and subjects as normalization constant is significantly important for ensuring better performances in the classification of new samples. It also must be considered that, advantageously, the normalization using the disclosed average RR method is not particularly demanding of computer capabilities.

After proving that the value used for normalizing new features values cannot be a random constant, we also compared the accuracy obtained using the proposed normalization versus using the normalization method currently used in pattern recognition methods—the feature equalization method, that implies the application of the following normalization along each feature:

$$x_N(i) = \frac{x(i) - \bar{x}}{\sigma}$$

Where $x_N(i)$ is the sample normalized value, $x(i)$ is each sample value, $\bar{x}$ is the average value across samples for a given feature, $\sigma$ is the standard deviation across samples for that feature.

In the table below is presented the accuracy per subject for a different group of 10 persons, using the proposed normalization and the features equalization method.

TABLE VI

Results obtained using the two method of normalization tested.

| Condition | Subject | Accuracy per Subject (%) | p-value (between conditions) |
|---|---|---|---|
| Normalization of test samples using the physiology-based normalization using average RR | Subject 1 | 100 | 0.178 |
| | Subject 2 | 100 | |
| | Subject 3 | 94.71 | |
| | Subject 4 | 98.94 | |
| | Subject 5 | 96.30 | |
| | Subject 6 | 99.47 | |
| | Subject 7 | 100 | |
| | Subject 8 | 95.77 | |
| | Subject 9 | 100 | |
| | Subject 10 | 88.89 | |
| | MEAN | 97.41 | |
| Features Equalization Method | Subject 1 | 100 | |
| | Subject 2 | 100 | |
| | Subject 3 | 98.41 | |
| | Subject 4 | 100 | |
| | Subject 5 | 95.77 | |
| | Subject 6 | 100 | |
| | Subject 7 | 100 | |
| | Subject 8 | 95.77 | |
| | Subject 9 | 100 | |
| | Subject 10 | 98.41 | |
| | MEAN | 98.84 | |

By observing the results obtained, we can conclude that, although a higher average accuracy across subjects was obtained for the features equalization method, the difference between accuracy values per individual using the normalization and the equalization method was not significant. This indicates that the improvement obtained using the equalization method is not significant, and considering that this method is much more computationally demanding in comparison with the proposed normalization—the first involves in the computation 26 constant values, while for applying the second one, it is only necessary a single constant value—it is more worthwhile applying the second one.

Taking those results in consideration, we found that the disclosed normalization method reveals to be more efficient in comparison with the ones used so far in the prior art.

The following pertains testing the robustness of the three features selected using other types of classifiers—i.e. classifier dependence. In order to conclude if the three features used in this method are really relevant and the normalization important for achieving good accuracies, we performed several tests using a Back-Propagation Neural Network (instead of the Support Vector Machines), for evaluating if the high performance values were due to the relevance of the features selected, or were related with the classifier selected to be applied in this problem.

Different configurations of the Neural Network were used in this topic (different proportions between train, validation and test sets; different number of layers). A different group of 10 persons was used here.

TABLE VII

Results obtained using a Back-Propagation Neural Network as classifier.

| Condition | Subject | Accuracy per Subject (%) | % Training (number of samples) | % Validation (number of samples) | % Test (number of samples) |
|---|---|---|---|---|---|
| a) Run 1-10 layers | Subject 1 | 100 | 70 (798) | 15 (171) | 15 (171) |
| | Subject 2 | 100 | | | |
| | Subject 3 | 69.00 | | | |
| | Subject 4 | 93.33 | | | |
| | Subject 5 | 80.00 | | | |
| | Subject 6 | 86.40 | | | |
| | Subject 7 | 100 | | | |
| | Subject 8 | 100 | | | |
| | Subject 9 | 100 | | | |
| | Subject 10 | 100 | | | |
| | MEAN | 92.87 | | | |
| b) Run 2-10 layers | Subject 1 | 100 | 70 (798) | 15 (171) | 15 (171) |
| | Subject 2 | 100 | | | |
| | Subject 3 | 80.00 | | | |
| | Subject 4 | 94.44 | | | |
| | Subject 5 | 100 | | | |
| | Subject 6 | 100 | | | |
| | Subject 7 | 100 | | | |
| | Subject 8 | 100 | | | |
| | Subject 9 | 100 | | | |
| | Subject 10 | 93.33 | | | |
| | MEAN | 96.77 | | | |
| c) Run 3-3 layers | Subject 1 | 100 | 70 (798) | 15 (171) | 15 (171) |
| | Subject 2 | 100 | | | |
| | Subject 3 | 90.90 | | | |
| | Subject 4 | 100 | | | |
| | Subject 5 | 93.33 | | | |
| | Subject 6 | 100 | | | |
| | Subject 7 | 100 | | | |
| | Subject 8 | 100 | | | |
| | Subject 9 | 100 | | | |
| | Subject 10 | 91.30 | | | |
| | MEAN | 97.55 | | | |
| d) Run 4-5 layers | Subject 1 | 100 | 70 (798) | 10 (114) | 20 (228) |
| | Subject 2 | 100 | | | |
| | Subject 3 | 90.00 | | | |
| | Subject 4 | 94.70 | | | |
| | Subject 5 | 100 | | | |

TABLE VII-continued

Results obtained using a Back-Propagation Neural Network as classifier.

| Condition | Subject | Accuracy per Subject (%) | % Training (number of samples) | % Validation (number of samples) | % Test (number of samples) |
|---|---|---|---|---|---|
| | Subject 6 | 97.10 | | | |
| | Subject 7 | 93.30 | | | |
| | Subject 8 | 100 | | | |
| | Subject 9 | 100 | | | |
| | Subject 10 | 88.60 | | | |
| | MEAN | 96.37 | | | |
| e) Run 5-10 layers | Subject 1 | 100 | 50 (627) | 20 (228) | 30 (285) |
| | Subject 2 | 100 | | | |
| | Subject 3 | 73.70 | | | |
| | Subject 4 | 95.50 | | | |
| | Subject 5 | 89.20 | | | |
| | Subject 6 | 100 | | | |
| | Subject 7 | 100 | | | |
| | Subject 8 | 93.80 | | | |
| | Subject 9 | 100 | | | |
| | Subject 10 | 94.30 | | | |
| | MEAN | 94.65 | | | |
| f) Run 6-3 layers | Subject 1 | 100 | 55 (627) | 10 (114) | 35 (399) |
| | Subject 2 | 100 | | | |
| | Subject 3 | 89.80 | | | |
| | Subject 4 | 97.10 | | | |
| | Subject 5 | 89.60 | | | |
| | Subject 6 | 100 | | | |
| | Subject 7 | 100 | | | |
| | Subject 8 | 97.00 | | | |
| | Subject 9 | 100 | | | |
| | Subject 10 | 92.70 | | | |
| | MEAN | 96.62 | | | |

We observed that similar results are obtained using a Neural Network in comparison with the SVM method. Concluding, the three features selected for this method and the normalization method proposed are really relevant for obtaining good performances, in general independently of the type of classifier included in the method, considering the tested classifiers which are preferable embodiments of the disclosure having shown advantageous results in combination with the previously mentioned steps.

The following pertains to comparing accuracy results obtained using only 3 features versus a higher number of features. Taking into account that the majority of the methods developed for solving this problem use much more features than we use here, we performed several tests in order to evaluate if the inclusion of more features (in addition to the three already selected) would significantly increase performance accuracy. We therefore evaluated the method performance using 13 features: temporal distance between points R and T (RT); between Q and T (QT); between S and T (ST); R and P (RP); between the point that marks the beginning of the P wave and point Q (bPQ); between the point that marks the beginning of the P wave and point P (bPP); between the point that marks the beginning of the P wave and point R (bPR); between the point that marks the beginning of the P wave and point S (bPS); between the point that marks the beginning of the P wave and point T (bPT); the amplitude difference between points R and P (RP amplitude); the amplitude difference between points R and S (RS amplitude); the amplitude difference between points R and Q (RQ amplitude); the amplitude difference between points R and T (RT amplitude). Accuracy values of using 3 or 13 features were compared.

TABLE VIII

Results obtained using 3 versus 13 features for the classification problem.

| Condition | Subject | Accuracy per Subject (%) | p-value (between conditions) |
|---|---|---|---|
| 3 features | Subject 1 | 100 | p = 0.06 |
| | Subject 2 | 100 | |
| | Subject 3 | 94.97 | |
| | Subject 4 | 98.89 | |
| | Subject 5 | 96.09 | |
| | Subject 6 | 99.44 | |
| | Subject 7 | 100 | |
| | Subject 8 | 97.21 | |
| | Subject 9 | 100 | |
| | Subject 10 | 91.62 | |
| | MEAN | 97.82 | |
| 13 features | Subject 1 | 94.97 | |
| | Subject 2 | 94.97 | |
| | Subject 3 | 92.73 | |
| | Subject 4 | 98.89 | |
| | Subject 5 | 95.53 | |
| | Subject 6 | 92.18 | |
| | Subject 7 | 91.06 | |
| | Subject 8 | 91.62 | |
| | Subject 9 | 93.29 | |
| | Subject 10 | 99.44 | |
| | MEAN | 94.47 | |

Taking into account the results of the table above, a slightly better performance is obtained using only 3 features in comparison with 13, although this improvement be not significant (p>0.05). Therefore, considering the computational cost associated with the two options, the first one (3 features) is notoriously more favourable.

It is disclosed a device and a method of recognizing a subject using only three characteristics extracted from its ECG waveform that allows fast recognition and high performance rates and low FRR. Due to its computational simplicity, the disclosed method can be embedded in a device, e.g. hardware modules with simple architectures, being capable of recognizing a subject using only 1 to 2 heartbeat waveforms (approximately 2 seconds). Two important attributes that characterize the method are the normalization that is involved in the classification scheme, and the three features selected for characterizing each individual—that are based on the ECG morphology. According with several tests performed, the normalization method included in this method ensures higher performance rates in comparison with the methods used so far. Accordingly, the three features selected here—distance measures ST, QT and RT—are indeed relevant, being capable of correctly identifying a subject, mostly independently of the type of the classifier used for the recognition task; being even much stronger and robust used together that in addition with other type of features (related with amplitude, for example).

The term "comprising" whenever used in this document is intended to indicate the presence of stated features, integers, steps, components, but not to preclude the presence or addition of one or more other features, integers, steps, components or groups thereof.

It is to be appreciated that certain embodiments of the disclosure as described herein may be incorporated as code (e.g., a software algorithm or program) residing in firmware and/or on computer useable medium having control logic for enabling execution on a computer system having a computer processor, such as any of the servers described herein. Such a computer system typically includes memory storage configured to provide output from execution of the code which configures a processor in accordance with the execution. The code can be arranged as firmware or software, and can be organized as a set of modules, including the various modules and methods described herein, such as discrete code modules, function calls, procedure calls or objects in an object-oriented programming environment. If implemented using modules, the code can comprise a single module or a plurality of modules that operate in cooperation with one another to configure the machine in which it is executed to perform the associated functions, as described herein. The above described embodiments are combinable.

The invention claimed is:

1. A method for identifying a person through an electrocardiogram(ECG) waveform, said method comprising:
    capturing ECG signals from a sample population including the person to be identified;
    computing ECG fiducial points Q, R, S and T of the sample population from the captured ECG signals;
    computing the ECG distances consisting of ECG distances ST, RT and QT, or any other three linear-combination distances of ST, RT and QT, from the computed ECG fiducial points Q, R, S and T of the sample population;
    computing an average of the ECG distance RR from the captured ECG signals from the sample population;
    normalizing the computed ECG distances ST, RT and QT of the sample population and of the person to be identified, using the average of the ECG distance RR;
    training a computer classification model on the normalized, computed sample population ECG distances;
    capturing an ECG signal from the person to be identified;
    computing the person's ECG fiducial points Q, R, S and T from the person's captured ECG signal;
    computing the ECG distances consisting of ECG distances ST, RT and QT, or the same three linear-combination distances of ST, RT and QT used when training the computer classification model, from the person's computed ECG fiducial points Q, R, S and T; and
    using the classification model with the person's normalized, computed ECG distances to identify the person to be identified within the sample population.

2. The method according to claim 1, further comprising computing ECG distances from the captured ECG signals of the sample population for up to a maximum of 25 to 60 heartbeat waveforms for each population member.

3. The method according to claim 1, further comprising computing ECG distances from the captured ECG signals of the person to be identified for 1 to 2 heartbeat waveforms.

4. The method according to claim 1, wherein computing the ECG distances ST, RT and QT of a heartbeat waveform includes:
    determining the fiducial points Q, R, S and T from the heartbeat waveform, and
    calculating the time intervals between S and T for ECG distance ST, between R and T for ECG distance RT, and between Q and T for ECG distance QT.

5. The method according to claim 1, wherein computing the each ECG distance RR in the sample population includes:
    determining the fiducial point R from the heartbeat waveform and the fiducial point R from the preceding heartbeat waveform, and
    calculating the time interval between the two fiducial points R for ECG distance RR.

6. The method according to claim 1, further comprising rejecting the computed ECG distances of a heartbeat waveform if the heartbeat waveform is determined to be a noisy waveform.

7. The method according to claim 6, wherein the heartbeat waveform is determined to be the noisy waveform if the following formula is verified:

$$QR \leq 0.075 \text{ s and } 0.200 \text{ s} < \frac{QT}{\sqrt{RR}} < 0.360 \text{ s}.$$

8. The method according to claim 7, wherein computing the ECG distances QR, QT and RR of the heartbeat waveform includes:
    determining the fiducial points Q, R and T from the heartbeat waveform,
    calculating the time intervals between Q and R for ECG distance QR, between Q and T for ECG distance QT,
    determining the fiducial point R from the preceding heartbeat waveform, and
    calculating the time interval between the two fiducial points R for ECG distance RR.

9. The method according to claim 1, further comprising filtering the captured ECG signal.

10. The method according to claim 1, further comprising for identifying the person using a plurality of heartbeats in the captured ECG signal, and selecting the person that was identified more frequently over said plurality of heartbeats.

11. A non-transitory storage media including program instructions for implementing a method for identifying a person through an electrocardiogram(ECG) waveform, the program instructions including instructions executable to carry out the method of claim 1.

12. A device for identifying a person through an electrocardiogram, ECG, waveform, said device comprising a non-transitory storage media according to claim 11.

13. The device according to claim 12, further comprising an ECG capture circuit and a digital data processor for carrying out said program instructions.

14. A method for identifying a person through an electrocardiogram(ECG) waveform, against a previously trained computer classification model using a sample population including the person to be identified, said method comprising:

capturing an ECG signal from the person to be identified;

computing the person's ECG fiducial points Q, R, S and T from the person's captured ECG signal;

computing the ECG distances consisting of ECG distances ST, RT and QT, or three linear-combination distances of ST, RT and QT previously used when training said computer classification model, from the person's computed ECG fiducial points Q, R, S and T;

normalizing the computed ECG distances ST, RT and QT of the sample population and of the person to be identified, using an average of the ECG distance RR; and using the classification model with the person's normalized, computed ECG distances to identify the person to be identified within the sample population, wherein the classification model was previously trained on sample population ECG distances consisting of ECG distances ST, RT and QT, or any other three linear-combination distances of ST, RT and QT, which were computed from the computed ECG fiducial points Q, R, S and T which were normalized, using the average of the ECG distance RR from computed ECG signals which were computed from captured ECG signals from the sample population, wherein the average of the ECG distance RR is obtained from captured ECG signals from the sample population.

15. The method according to claim 14, further comprising computing ECG distances from the captured ECG signals of the sample population for up to a maximum of 25 to 60 heartbeat waveforms for each population member.

16. The method according to claim 14, wherein computing the ECG distances ST, RT and QT of a heartbeat waveform includes:

determining the fiducial points Q, R, S and T from the heartbeat waveform, and calculating the time intervals between S and T for ECG distance ST, between R and T for ECG distance RT, and between Q and T for ECG distance QT.

17. The method according to claim 14, wherein a heartbeat waveform is determined to be a noisy waveform if the following formula is verified:

$$QR \leq 0.075 \text{ s and } 0.200 \text{ s} < \frac{QT}{\sqrt{RR}} < 0.360 \text{ s}.$$

* * * * *